(12) United States Patent
Chang et al.

(10) Patent No.: US 9,962,282 B2
(45) Date of Patent: May 8, 2018

(54) FILM FOR UROSTOMY POUCH BAFFLE AND POUCH USING SAME

(71) Applicant: Hollister Incorporated, Libertyville, IL (US)

(72) Inventors: Moh-Ching Oliver Chang, Lake in the Hills, IL (US); Senan Z. Ozbag, Elk Grove Village, IL (US)

(73) Assignee: HOLLISTER INCORPORATED, Libertyville, IL (US)

(*) Notice: Subject to any disclaimer, the term of this patent is extended or adjusted under 35 U.S.C. 154(b) by 611 days.

(21) Appl. No.: 14/337,888

(22) Filed: Jul. 22, 2014

(65) Prior Publication Data
US 2015/0190271 A1    Jul. 9, 2015

Related U.S. Application Data

(60) Provisional application No. 61/924,513, filed on Jan. 7, 2014.

(51) Int. Cl.
| | |
|---|---|
| *A61F 5/445* | (2006.01) |
| *B31B 27/00* | (2006.01) |
| *B31B 70/00* | (2017.01) |
| *B31B 150/00* | (2017.01) |
| *B31B 170/00* | (2017.01) |
| *B31B 160/20* | (2017.01) |

(52) U.S. Cl.
CPC .............. *A61F 5/445* (2013.01); *B31B 70/00* (2017.08); *B31B 2150/00* (2017.08); *B31B 2160/20* (2017.08); *B31B 2170/00* (2017.08)

(58) Field of Classification Search
CPC combination set(s) only.
See application file for complete search history.

(56) References Cited

U.S. PATENT DOCUMENTS

| | | | | |
|---|---|---|---|---|
| 4,084,590 A | * | 4/1978 | Caraway | A61F 5/445 604/335 |
| 4,300,560 A | * | 11/1981 | Steer | A61F 5/445 604/335 |
| 4,519,797 A | * | 5/1985 | Hall | A61F 5/445 604/332 |

(Continued)

FOREIGN PATENT DOCUMENTS

| | | |
|---|---|---|
| WO | 2012069299 A1 | 5/2012 |
| WO | WO 2012069299 A1 * | 5/2012 ............. A61F 5/445 |

OTHER PUBLICATIONS

Anil K. Bhowmick and Howard L. Stephens: "Handbook of Elastomers, Second Edition, Revised and Explained", published 2001, Retrieved from the Internet: URL:books.google.de/books?isbn=0824703839839.

(Continued)

*Primary Examiner* — Tatyana Zalukaeva
*Assistant Examiner* — Guy K Townsend
(74) *Attorney, Agent, or Firm* — Levenfeld Pearlstein, LLC

(57) ABSTRACT

A urostomy pouch includes a baffle member, which is formed using multilayer film sheets. The multilayer film includes an inner layer comprising polypropylene and styrenic block copolymer, and an outer layer comprising ethyl methyl acrylate copolymer (EMA). The multilayer film sheets are arranged such that the inner layers face each other and are ultrasonically sealed along their longitudinal edges to form a tubular-shaped baffle member.

16 Claims, 2 Drawing Sheets

(56) References Cited

U.S. PATENT DOCUMENTS

| | | | | |
|---|---|---|---|---|
| 4,604,095 | A * | 8/1986 | Samuelsen | A61F 5/4405 604/323 |
| 5,567,489 | A * | 10/1996 | Allen | A61F 5/445 428/34.1 |
| 5,681,627 | A * | 10/1997 | Mueller | B32B 7/12 428/35.2 |
| 5,846,620 | A * | 12/1998 | Compton | B32B 27/08 428/35.7 |
| 6,143,383 | A * | 11/2000 | Giori | A61L 28/0015 428/35.2 |
| 6,258,423 | B1 * | 7/2001 | Giori | A61F 5/445 428/220 |
| 6,451,912 | B1 * | 9/2002 | Kelch | B32B 27/06 525/179 |
| 6,455,161 | B1 * | 9/2002 | Regnier | B32B 27/28 428/412 |
| 6,558,809 | B1 * | 5/2003 | Kelch | B32B 27/08 428/520 |
| 6,685,683 | B1 * | 2/2004 | Clok | A61F 5/443 604/344 |
| 6,858,313 | B2 * | 2/2005 | Musco | B29C 47/0026 383/109 |
| 6,946,182 | B1 * | 9/2005 | Allgeuer | B29C 43/222 264/134 |
| 7,270,860 | B2 * | 9/2007 | Giori | A61F 5/445 428/35.7 |
| 7,476,220 | B2 * | 1/2009 | Lillegaard | A61F 5/4404 4/144.2 |
| 9,119,727 | B2 * | 9/2015 | Hannan | A61F 5/4405 |
| 2002/0025394 | A1 * | 2/2002 | Bradfute | B32B 27/30 428/34.9 |
| 2003/0014023 | A1 * | 1/2003 | Kanbara | A61F 5/441 604/333 |
| 2003/0064182 | A1 * | 4/2003 | Giori | B32B 27/32 428/35.2 |
| 2009/0163883 | A1 * | 6/2009 | Christensen | A61F 5/4405 604/328 |
| 2009/0317611 | A1 * | 12/2009 | Mueller | A61J 1/10 428/212 |
| 2011/0125114 | A1 * | 5/2011 | Bekele | A61F 5/445 604/332 |
| 2012/0258326 | A1 * | 10/2012 | Pham | B32B 25/08 428/518 |
| 2013/0053802 | A1 * | 2/2013 | Maidl | A61F 5/445 604/332 |
| 2014/0163497 | A1 * | 6/2014 | Hannan | A61F 5/4405 604/344 |
| 2015/0190271 | A1 * | 7/2015 | Chang | A61F 5/445 604/332 |

OTHER PUBLICATIONS

Written Opinion and International Search Report for PCT/US2014/047855 dated Nov. 7, 2014.

* cited by examiner

FILM FOR UROSTOMY POUCH BAFFLE AND POUCH USING SAME

CROSS-REFERENCE TO RELATED APPLICATION DATA

This application claims the benefit of priority of Provisional U.S. Patent Application Ser. No. 61/924,513, filed Jan. 7, 2014 entitled, "FILM FOR UROSTOMY POUCH BAFFLE AND POUCH USING SAME."

BACKGROUND

The present disclosure is directed to a pouch for collecting biological fluids (such as excretions from a surgically-created stoma), such as, for example, a urostomy pouch for collecting liquid human waste. More particularly, the present disclosure pertains to a baffle member of a urostomy pouch. However, as the skilled person will recognize, the applicability of the present disclosure is not limited to the field of urostomy pouches, as it is also applicable to other types of devices, such as pouches for collection of ileostomy output, wound drainage pouches, etc. For the sake of brevity, the present disclosure will focus on urostomy pouches.

A urostomy pouch is a medical device that provides a means for collecting liquid waste output from an opening into the urinary system that is diverted externally of the body through a stoma.

For obvious reasons, users of a urostomy pouch are very concerned about privacy and discreteness of such a urostomy pouch. However, a urostomy pouch often bulges as it becomes filled with liquid waste and becomes difficult to conceal. Further, the liquid waste collected in the pouch has a tendency to lap or slosh when the user moves and such lapping or sloshing may make undesirable sounds.

Thus, to reduce bulging and sloshing of liquid waste in a pouch, a urostomy pouch including a baffle member was introduced. For example, WO 2012/069299, which is assigned to the Applicant of the present application and incorporated herein by reference, discloses a urostomy pouch including a baffle member. This reference discloses a tubular baffle member that is attached to the pouch walls. The reference also discloses that the baffle member can be formed of a two-layer film including a polypropylene layer and a polyethylene layer. However, it was discovered that using such a two-layer film composition may present difficulties in controlling process tolerances and may result in increased production costs.

Accordingly, there is a need for a film for a baffle member in a urostomy pouch that can provide improved process consistency and produce high quality urostomy pouches.

BRIEF SUMMARY

A urostomy pouch is provided with a baffle member to reduce bulging of the pouch as the pouch becomes filled with liquid body waste and to reduce sloshing of liquid in the pouch. The baffle member may be formed with a two-layer film including an inner layer formed from a first thermoplastic composition comprising polypropylene and styrenic block copolymer, and an outer layer formed from a second thermoplastic composition, in which the second thermoplastic composition has a melting temperature that is at least 5° C. lower than that of the first thermoplastic composition. It was discovered that by using such a two-layer film and ultrasonic sealing methods, the quality and the consistency of the process for making the urostomy pouch with a baffle member can be improved significantly.

In one aspect, a pouch for collecting biological fluids including a body side wall and a distal side wall defining a collection chamber therebetween is provided. The pouch also includes an inlet opening, which is provided in the body side wall, and a baffle member arranged in the collection chamber. The baffle member may be formed from two sheets of a multilayer film. The multilayer film includes an inner layer formed from a first thermoplastic composition comprising polypropylene and styrenic block copolymer, and an outer layer formed from a second thermoplastic composition, in which the second thermoplastic composition has a melting temperature that is at least 5° C. lower than that of the first thermoplastic composition. The two sheets may be arranged such that the inner layers face each other and the outer layers face the body side wall and the distal side wall, in which the inner layers are attached to each other and each of the outer layers is attached to the body side wall or the distal side wall.

In an embodiment, the multilayer film may be a two-layer film including an inner layer comprising about 70 wt. % to about 99 wt. % polypropylene and about 1 wt. % to about 30 wt. % styrenic block copolymer, and an outer layer comprising at least about 90 wt. % of a thermoplastic polymer, which may be selected from low density polyethylene (LDPE), linear low density polyethylene (LLDPE), ethylene vinyl acetate (EVA), ethylene methyl acrylate copolymer (EMA), atactic polypropylene (PP), and polypropylene-polyethylene (PP-PE) copolymer. However, suitable thermoplastic polymers for the outer layer are not limited to these polymers and other similar thermoplastic polymers having a melting temperature that is at least 5° C. lower than that of the first thermoplastic composition may also be used. For example, the two layer film may include an inner layer comprising about 85 wt. % to about 95 wt. % polypropylene and about 5 wt. % to about 15 wt. % styrene isoprene block copolymer, and an outer layer comprising about 95 wt. % to about 100 wt. % EMA.

Each of the two sheets of the multilayer film may have a rectangular-like shape having similar size and dimensions. The two sheets may be arranged over each other, such that the inner layers of the sheets face each other and outer layers face the body side wall or the distal side wall. The two sheets may be ultrasonically sealed to each other about their longitudinal edges to form a tubular-shaped baffle member. Preferably, each of the ultrasonically sealed edges has a seal strength of about 1.5 lb./in to about 3.5 lb./in when tested using a tensile testing machine at a constant separation rate of about 12.0±0.5 in/min.

Each of the two sheets may be heat sealed to the body side wall or the distal side wall via at least one attachment line. In one embodiment, one of the two sheets may be heat sealed to the body side wall via a pair of attachment lines, which are generally linear and non-parallel with a wider distance between them at the lower ends than at the upper ends. The attachment lines may be curved smoothly at their end portions in an obtuse angle and may be arranged symmetrically about the longitudinal center line of the pouch. The other sheet may be heat sealed to the distal side wall via a single continuous attachment line including smooth radiused upper and lower portions.

In some embodiments, the pouch may also include an anti-reflux film provided in an upper portion of the pouch between the body side wall and the distal side wall. Further, the pouch may also include a valve, which is provided at an opening in a bottom end of the ostomy pouch.

In the any of the above described embodiments, the pouch may be a urostomy pouch configured to collect liquid body waste.

In another aspect, a method of making pouch for collecting biological fluids including a body side wall, a distal side wall and a collection chamber defined therebetween is provided. The method includes the steps of providing an inlet opening in the body side wall and providing a baffle member. The baffle member may be formed using two sheets of a multilayer film. The multilayer film may include an inner layer formed from a first thermoplastic composition comprising polypropylene and styrenic block copolymer, and an outer layer formed from a second thermoplastic composition, in which the second thermoplastic composition has a melting temperature that is at least 5° C. lower than that of the first thermoplastic composition. The two sheets are arranged such that the inner layers face each other and the outer layers face the body side wall and the distal side wall. The step of forming the baffle member includes sealing the sheets along their longitudinal peripheral edges via ultrasonic welding to form a tubular baffle member.

Preferably, the sheets are ultrasonically sealed together such that each of the sealed peripheral edges has a seal strength of about 1.5 lb./in to about 3.5 lb./in when tested using a tensile testing machine at a constant separation rate of about 12.0±0.5 in/min.

Further, the method may include arranging the baffle member in the collection chamber, such that the outer layer of one of the sheets is adjacent the body side wall and the outer layer of the other sheet is adjacent the distal side wall, and heat sealing one of the sheets to the body side wall via at least one attachment line, and heat sealing the other sheet to the distal side wall via at least one attachment line.

In one embodiment, one of the sheets may be heat sealed to the body side wall via a pair of attachment lines, which are generally linear and non-parallel with a wider distance between them at the lower ends than at the upper ends. The attachment lines may be curved smoothly proximate their end portions in an obtuse angle, and the attachment lines may be symmetrical about the longitudinal center line of the pouch. The other sheet may be heat sealed to the distal side wall via a single continuous attachment line including smooth radiused upper and lower portions.

The baffle member may be formed using a two-layer film including an inner layer comprising about 70 wt. % to about 99 wt. % polypropylene and about 1 wt. % to about 30 wt. % styrenic block copolymer, and an outer layer comprising at least about 90 wt. % of a thermoplastic polymer, which may be selected from LDPE, LLDPE, EVA, EMA, atactic PP, and PP-PE copolymer. However, suitable thermoplastic polymers for the outer layer are not limited to these polymers and other polyethylene based polymers and polypropylene based polymers having a melting temperature that is at least 5° C. lower than that of the first thermoplastic composition may also be used. For example, the baffle member may be formed using a two layer film including an inner layer comprising about 85 wt. % to about 95 wt. % polypropylene and about 5 wt. % to about 15 wt. % styrene isoprene block copolymer, and an outer layer comprising about 95 wt. % to about 100 wt. % EMA.

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 2A:
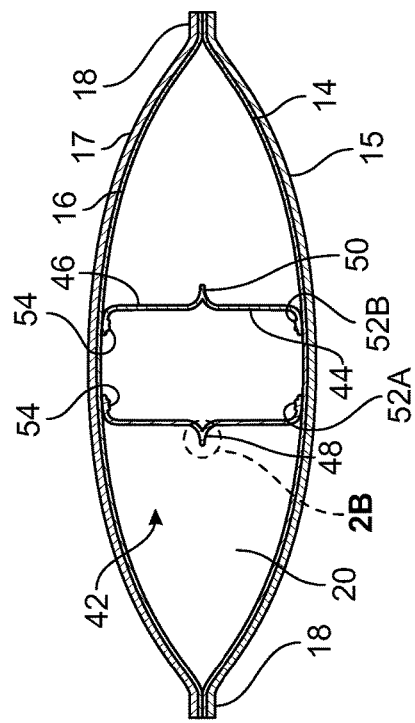
FIG. 2A is a cross sectional view taken along line 2A-2A of FIG. 1.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Figure 2B:
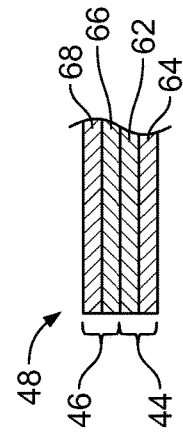
FIG. 2B is an enlarged view of the baffle member taken at 2B of FIG. 2A.
Figure 1:
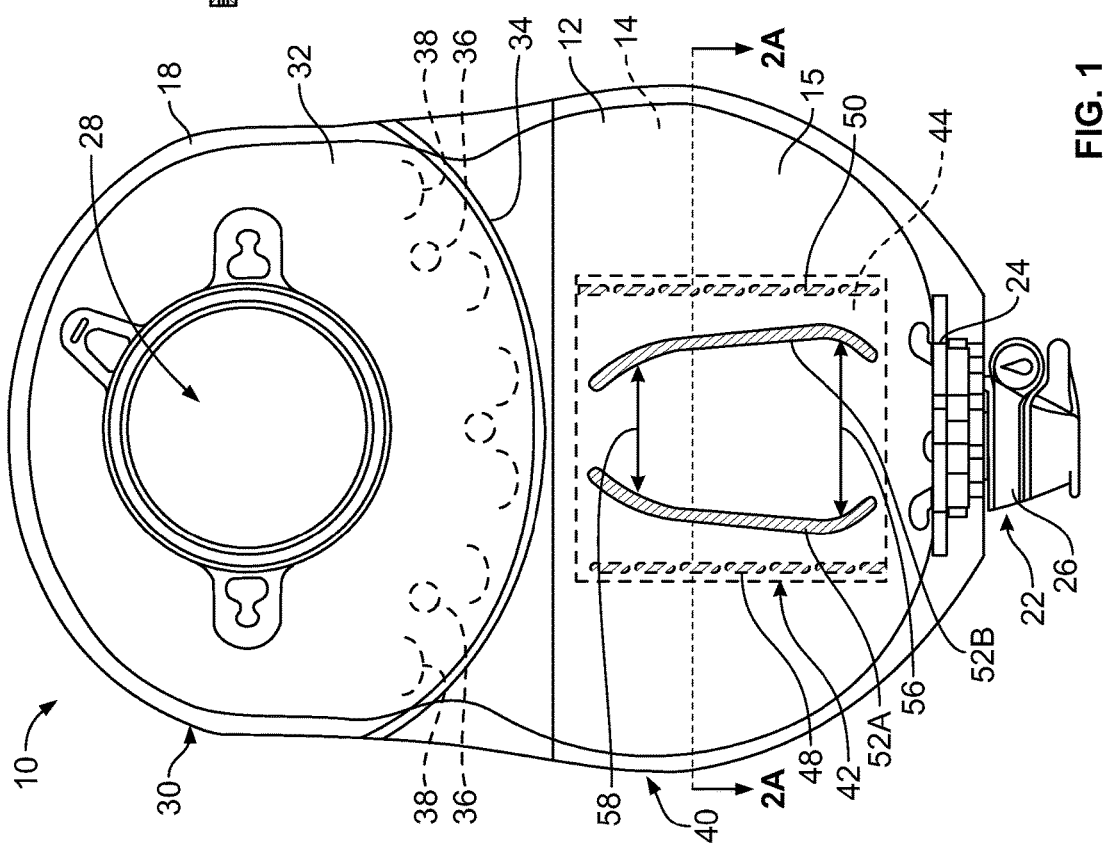
FIG. 1 is a body side view of a urostomy pouch including a baffle member according to an embodiment.
Figure 3:
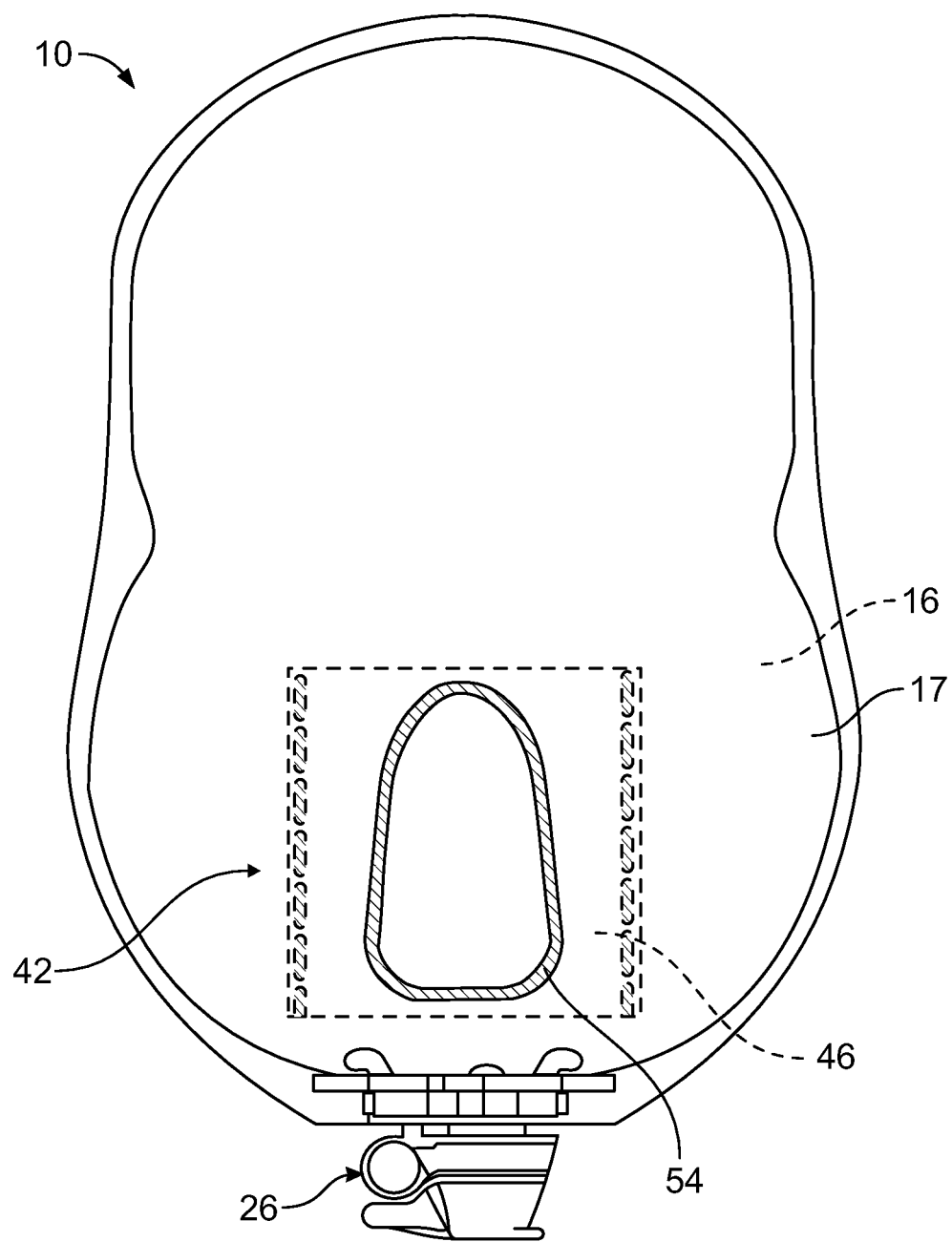
FIG. 3 is a distal side view of the urostomy pouch of FIG. 1.

Referring now to the figures and briefly first to FIGS. 1-3, there is shown an embodiment of a urostomy pouch 10 having a body 12 formed by, for example, sealing two films 14, 16 to one another about their respective peripheries 18 to define a collection chamber 20. The pouch film 14 is also referred to herein as a first wall or a body side wall. The second wall 16 is also referred to herein as a second wall or a distal side wall. The pouch 10 may also be formed from a tubular structure sealed around its open peripheral ends to define an interior chamber.

The bottom 22 of the pouch 10 may include an opening 24 into which a valve 26 may be fitted and secured. The films 14, 16 may be sealed to one another by methods such a heat sealing and the like; the valve 26 may be similarly sealed to the pouch 10 at the bottom opening 24. Suitable methods for sealing the pouch walls/films 14, 16 to one another and valve 26 to the pouch films 14, 16 will be recognized by those skilled in the art. The pouch 10 may be provided with non-woven layers 15, 17. Although the pouch 10 shown in FIGS. 1-3 is provided with a non-woven layer 15, 17 on each of the body side and distal side of the pouch 10, in other embodiments, a non-woven layer may only be provided on the body side or on the distal side of the pouch or may not be provided.

In the top section 30 of the pouch 10, an inlet opening 28 is provided in the first wall 14, through which body waste enters the pouch 10 from a stoma. An intermediate anti-reflux film 32 is provided in the top section 30 between the first and second walls 14, 16. The anti-reflux film 32 may be sealed to the first wall 14 at the lower periphery of the anti-reflux film 32 at a lower anti-reflux seal 34 and the anti-reflux film 32 may also be sealed to the first and second walls 14, 16 at their common periphery 18. The anti-reflux film 32 covers the opening 28, and the lower anti-reflux seal 34 is provided at a certain distance from the opening 28. The lower anti-reflux seal 34 is preferably provided substantially concentric with the inlet opening 28, in which the lower anti-reflux seal 34 expands across the pouch 10 with an upwardly oriented concave shape.

A number of adhesion areas, such as spot welds 36 may be provided in a similar concave arcuate configuration across the pouch 10. The spot welds 36 can be about the same distance above the lower anti-reflux seal 34. A plurality of slits 38 may be provided in the anti-reflux film 32 between the lower anti-reflux seal 34 and the spot welds 36. The spot welds 36 seal the anti-reflux film 32 to at least the body side wall 14, and may also seal the anti-reflux film 32 to the distal side wall 16. When the anti-reflux film 32 is sealed to the both pouch walls 14, 16, the anti-reflux film 32 may function to reduce bulging of the pouch 10 as it becomes filled with liquid body waste.

In the pouch embodiment including such an anti-reflux film 32, a collection chamber 20 for storing liquid body waste entering the pouch 10 through the inlet opening 28 is provide below the lower anti-reflux seal 34 and between the anti-reflux film 32 and the second wall 16.

In the lower section 40 of the pouch 10, a baffle member 42 may be provided inside the collection chamber 20 between the first and second walls 14, 16. The baffle member 42 may be formed using two sheets of a baffle film 44, 46, which may be joined together by longitudinal attachments 48, 50 to form a tubular structure. The tubular structure may be provided with a vertical orientation. Two sheets of the baffle film 44, 46 are also referred to herein as a first baffle film 44 and a second baffle film 46. The first and second baffle films 44, 46 may be attached to the first and the second walls 14, 16, respectively.

In the embodiment shown, the baffle member 42 may be attached to the pouch walls 14, 16 by attachment lines 52A, 52B, 54. The first baffle film 44 may be sealed to the first pouch wall 14 via a pair of attachment lines 52A, 52B, while the second baffle film 46 may be sealed to the second pouch wall 16 via a single continuous attachment line 54. As best seen in FIG. 1, the two attachment lines 52A and 52B may be generally linear and non-parallel with a wider distance between them at their lower ends 56 than at the upper ends 58. The end portions of the attachment lines 52A and 52B are curved smoothly in a large obtuse angle, preferably greater than 120°, to reduce a risk of seal failure during use. The two attachment lines 52A and 52B may be symmetrical about the longitudinal center line of the pouch 10. The attachment line 54, as best seen in FIG. 3, is similarly shaped as the pair of attachment lines 52A, 52B, except the end portions are closed to form a single attachment line 54. The attachment lines may be arranged such that the attachment line 54 and the pair of attachment lines 52A, 52B closely overlap each other.

In other embodiments, the baffle films 44, 46 may be attached to the pouch walls 14, 16 via identical attachment lines. For example, each of the baffle films 44, 46 may be attached via a pair of attachment lines similar to the attachment lines 52A, 52B, or via a single continuous attachment line similar to the attachment line 54.

The baffle films 44, 46 may be formed from a two-layer film. Each layer of the two-layer film may be formed from a different thermoplastic material, in which the layer on the side facing the inside of the baffle member 42 is formed using a thermoplastic material having a higher melting point than that of the other layer facing the pouch walls. In such a configuration, the heat or energy imparted to the films when welding the baffle films 44, 46 to the pouch walls 14, 16 is not sufficiently high to weld through the inner layers of the baffle films 44, 46. Thus, the baffle member 42 remains open while the baffle films 44, 46 are sealed to the pouch walls 14, 16. That is, welding will not go all the way through and seal together the baffle films 44, 46 along the welding lines that seal the baffle films 44, 46 to the pouch walls 14, 16. In one embodiment, the baffle film 44, 46 may include an inner layer comprising polypropylene and an outer layer comprising polyethylene. For example, the inner layer facing the inside of the baffle member 42 may be formed from a polypropylene having a melting point of about 130° C.-165° C., whereas the outer layer that is welded to the pouch walls 14, 16 is formed from a polyethylene having a melting point of about 110° C.

In a baffle member made using such a two-layer film, the baffle films are arranged such that the inner layers face each other and are sealed together along longitudinal peripheral edges to form a tubular baffle member. In the embodiment shown in FIG. 2, the baffle films 44, 46 are welded together at the attachments 48, 50. Thus, when the above discussed two-layer film embodiment is used for the baffle films 44, 46, the polypropylene inner layers may be seal together via heat welding or ultrasonic welding. However, it was discovered that a heat welding process using a polyethylene/polypropylene two-layer film was difficult to control and resulted in a high production process variance, which translated into a greater number of rejected pouches and a high manufacturing cost.

After extensive research, it was discovered that a two-layer film including an inner layer formed from a polymer composition comprising a polypropylene and a styrenic block copolymer, and an outer layer formed from a polymeric composition having a melting temperature that is at least 5° C. lower than that of the polymeric composition of the inner layer, in conjunction with appropriate ultrasonic welding methods can be used for making the baffle member 42 and to provide high quality pouches with surprisingly high process consistency.

In preferred embodiments, the baffle film 44, 46 may be formed from a two-layer film including an inner layer formed from a polymer composition comprising about 30 wt. % to about 99 wt. % polypropylene and about 1 wt. % to about 70 wt. % styrenic block copolymer, preferably about 70 wt. % to about 95 wt. % polypropylene and about 5 wt. % to about 30 wt. % styrenic block copolymer, and more preferably about 85 wt. % to about 95 wt. % polypropylene and about 5 wt. % to about 15 wt. % styrenic block copolymer, and an outer layer comprising at least 90 wt. % of a thermoplastic polymer having a melting temperature that is at least about 5° C. lower than that of the polymeric composition for the inner layer. Suitable thermoplastic polymers for the outer layer include, but are not limited to, polyethylene based polymers, such as low density polyethylene (LDPE), linear low density polyethylene (LLDPE), ethylene vinyl acetate (EVA), and ethylene methyl acrylate copolymer (EMA), and polypropylene based polymers, such as atactic polypropylene (PP) and polypropylene-polyethylene (PP-PE) copolymer. The polypropylene in the polymer composition for inner layer may be homo-polypropylene or co-polypropylene.

In one embodiment, the two-layer baffle film 44, 46 may include an inner layer 62, 66 formed from a polymeric blend comprising about 90 wt. % polypropylene, such as Borealis® RD735CF from Borealis AG having a melting temperature of about 148° C. and about 10 wt. % styrene isoprene block copolymer, such as Hybrar® 7125 from Kuraray, and an outer layer 64 comprising about 99 wt. % EMA, such as Lotryl® 18MA02 from Arkema and about 1 wt. % of an antislip master batch, such as Polybatch® SAB1982VA from Schulman Inc. To form the baffle member 42, two sheets of two-layer baffle film 44, 46 are arranged in the pouch 10, such that the inner layers 62, 66 face each other, while the outer layers 64, 68 face pouch walls 14, 16, respectively. As discussed previously, the baffle films 44, 46 are sealed to the pouch walls 14, 16, respectively, via heat welding at the attachment lines 52A, 52B, 54. Since the inner layers 62, 66 are formed from a thermoplastic material having a relatively higher melting point than that of the outer layers 64, 68, the heat welding does not weld through the inner layers 62, 66 of the baffle films 44, 46. The longitudinal edges of the baffle films 44, 46 are sealed together via ultrasonic welding in a longitudinal pattern 48, 50, as shown in FIGS. 1 and 2. Preferably, each of the longitudinal edges 44, 46 has a seal strength of about 1.5 lb./in to about 3.5 lb./in when tested using a tensile testing machine with a constant jaw separation rate of about 12.0±0.5 in/min.

Examples and Test Results

Eight different two-layer film constructions were prepared and tested for their ultrasonic seal strength and process consistency.

TABLE 1

Two-Layer Film Constructions

| Film # | Inner Layer | Outer Layer |
|---|---|---|
| Control | polyethylene terpolymer | polypropylene |
| 293-1 | 99% Hytrel ® 4556 + 1% Polybatch ® SAB 1982VA (32 μm) | EMAC ® 2207 (32 μm) |
| 293-2 | 49% Hytrel ® 4556 + 50% Hytrel ® 5556 + 1% Polybatch ® SAB 1982VA (32 μm) | EMAC ® 2207 (32 μm) |
| 293-3 | 99% Hytrel ® 5556 + 1% Polybatch ® SAB 1982VA (32 μm) | EMAC ® 2207 (32 μm) |
| 293-4 | 100% Borealis ® RD735CF (29 μm) | 99% Lotryl ® 18MA02 + 1% Polybatch ® SAB1982VA (29 μm) |
| 293-5 | 90% Borealis ® RD735CF + 10% Vistamaxx ® 3980FL (29 μm) | 99% Lotryl ® 18MA02 + 1% Polybatch ® SAB1982VA (29 μm) |
| 293-6 | 90% Borealis ® RD735CF + 10% Hybrar ® 7125 (29 μm) | 99% Lotryl ® 18MA02 + 1% Polybatch ® SAB1982VA (29 μm) |
| 293-7 | 100% Borealis ® RD735CF (19 μm) | 99% Lotryl ® 18MA02 + 1% Polybatch ® SAB1982VA (39 μm) |

As summarized in Table 1, the Control film included an inner layer formed from polyethylene terpolymer and an outer layer formed from polypropylene.

Film#293-1 included an inner layer having a thickness of about 32 μm and comprising about 99 wt. % Hytrel® 4556 from DuPont (copolyester) and about 1 wt. % Polybatch® SAB 1982VA (antislip master batch), and an outer layer having a thickness of about 32 μm and comprising about 100 wt. % EMAC® 2207 from Westlake Chemical (EMA).

Film#293-2 included an inner layer having a thickness of about 32 μm and comprising about 49 wt. % Hytrel® 4556 (copolyester), 50 wt. % Hytrel® 5556 (copolyester), and about 1 wt. % Polybatch® SAB 1982VA (antislip master batch), and an outer layer having a thickness of about 32 μm and comprising about 100 wt. % EMAC® 2207 (EMA).

Film#293-3 included an inner layer having a thickness of about 32 μm and comprising about 99 wt. % Hytrel® 5556 (copolyester) and about 1 wt. % Polybatch® SAB 1982VA (antislip master batch), and an outer layer having a thickness of about 32 μm and comprising about 100 wt. % from EMAC® 2207 (EMA).

Film#293-4 included an inner layer having a thickness of about 29 μm and comprising about 100 wt. % Borealis® RD735CF (polypropylene), and an outer layer having a thickness of about 29 μm and comprising about 99 wt. % Lotryl® 18MA02 (EMA) and about 1 wt. % Polybatch® SAB1982VA (antislip master batch).

Film#293-5 included an inner layer having a thickness of about 29 μm and comprising about 90 wt. % Borealis® RD735CF (polypropylene) and about 10 wt. % Vistamaxx® 3980FL from ExxonMobile Chemical (polypropylene-polyethylene copolymer), and an outer layer having a thickness of about 29 μm and comprising about 99 wt. % Lotryl® 18MA02 (EMA) and about 1 wt. % Polybatch® SAB1982VA (antislip master batch).

Film#293-6 included an inner layer having a thickness of about 29 μm and comprising about 90 wt. % Borealis® RD735CF (polypropylene) and about 10 wt. % Hybrar® 7125 (styrene isoprene block copolymer), and an outer layer having a thickness of about 29 μm and comprising about 99 wt. % Lotryl® 18MA02 (EMA) and about 1 wt. % Polybatch® SAB1982VA (antislip master batch).

Film#293-7 included an inner layer having a thickness of about 19 μm and comprising about 100 wt. % Borealis® RD735CF (polypropylene), and an outer layer having a thickness of about 39 μm and comprising about 99 wt. % Lotryl® 18MA02 (EMA) and about 1 wt. % Polybatch® SAB1982VA (antislip master batch).

Five samples of each of the two-layer film constructions were prepared by using two sheets of the two-layer film and sealing their longitudinal edges via a ultrasonic welding such that the two inner layers are seal together in the longitudinal pattern similar to the ultrasonic welding attachments 48, 50 in FIG. 1. The samples were tested for their ultrasonic seal performance using a tensile testing machine at a constant jaw separation rate of about 12.0±0.5 inches/min. The seal strength test data are summarized in TABLE 2 below.

TABLE 2

Ultrasonic Seal Strength Test Results for Two-Layer Films

| Unit: lb./in | | | Sample # 1 | | Sample # 2 | | Sample # 3 | | Sample # 4 | | Sample # 5 | |
|---|---|---|---|---|---|---|---|---|---|---|---|---|
| FILM# | | | Left | Right | Left | Right | Left | Right | Left | Right | Left | Right |
| Control | Ave. | | 2.330 | 2.691 | 2.623 | 2.669 | 2.750 | 2.826 | 2.625 | 2.620 | 2.676 | 2.544 |
| | SD | | 0.219 | 0.377 | 0.376 | 0.308 | 0.308 | 0.429 | 0.365 | 0.355 | 0.237 | 0.402 |
| | Min | | 1.737 | 1.695 | 1.617 | 1.723 | 1.982 | 1.497 | 1.618 | 1.447 | 1.856 | 1.680 |
| | Max | | 2.776 | 3.332 | 3.276 | 3.355 | 3.296 | 3.463 | 3.239 | 3.238 | 3.068 | 3.170 |
| | Ppk | | 1.26 | 0.72 | 0.78 | 0.90 | 0.81 | 0.52 | 0.80 | 0.83 | 1.16 | 0.79 |
| | Visual | | Accept | | Accept | | Accept | | Accept | | Accept | |
| 293-1 | Ave. | | 0.866 | 1.292 | 1.205 | 1.621 | 1.284 | 1.250 | 1.536 | 1.273 | 1.256 | 0.850 |
| | SD | | 0.112 | 0.185 | 0.215 | 0.248 | 0.246 | 0.215 | 0.258 | 0.204 | 0.259 | 0.197 |
| | Min | | 0.657 | 0.982 | 0.852 | 1.116 | 0.993 | 0.711 | 1.106 | 0.870 | 0.838 | 0.510 |
| | Max | | 1.217 | 1.731 | 1.655 | 2.144 | 2.114 | 1.704 | 2.194 | 1.774 | 1.824 | 1.227 |
| | Ppk | | −1.89 | −0.37 | −0.47 | 0.16 | −0.29 | −0.39 | 0.05 | −0.37 | −0.31 | −1.10 |
| | Visual | | Accept | | Accept | | Reject: pleats | | Reject: pleats | | Reject: pleats | |

TABLE 2-continued

Ultrasonic Seal Strength Test Results for Two-Layer Films

Unit: lb./in

|  |  | Sample # 1 | | Sample # 2 | | Sample # 3 | | Sample # 4 | | Sample # 5 | |
|---|---|---|---|---|---|---|---|---|---|---|---|
| 293-2 | Ave. | 0.751 | 1.561 | 1.549 | 2.021 | 1.663 | 1.756 | 1.875 | 1.525 | 1.338 | 0.766 |
| | SD | 0.137 | 0.191 | 0.276 | 0.210 | 0.270 | 0.244 | 0.216 | 0.348 | 0.251 | 0.293 |
| | Min | 0.504 | 1.157 | 1.075 | 1.617 | 1.103 | 1.260 | 1.376 | 0.932 | 0.912 | 0.346 |
| | Max | 1.068 | 1.997 | 2.175 | 2.468 | 2.171 | 2.293 | 2.240 | 2.100 | 1.787 | 1.252 |
| | Ppk | −1.82 | 0.11 | 0.06 | 0.83 | 0.20 | 0.35 | 0.58 | 0.02 | −0.22 | −0.84 |
| | Visual | Accept | | Accept | | Accept | | Accept | | Accept | |
| 293-3 | Ave. | 0.778 | 1.673 | 1.560 | 2.142 | 1.849 | 1.717 | 1.861 | 1.524 | 1.388 | 0.712 |
| | SD | 0.153 | 0.237 | 0.250 | 0.255 | 0.224 | 0.183 | 0.221 | 0.232 | 0.210 | 0.163 |
| | Min | 0.503 | 0.911 | 1.106 | 1.602 | 1.453 | 1.402 | 1.118 | 1.022 | 1.011 | 0.490 |
| | Max | 1.114 | 2.063 | 2.088 | 2.626 | 2.366 | 2.198 | 2.346 | 1.987 | 1.912 | 1.317 |
| | Ppk | −1.58 | 0.24 | 0.08 | 0.84 | 0.52 | 0.40 | 0.54 | 0.03 | −0.18 | −1.61 |
| | Visual | Accept | | Accept | | Accept | | Accept | | Accept | |
| 293-4 | Ave. | 2.270 | 2.499 | 2.517 | 2.597 | 2.553 | 2.539 | 2.556 | 2.634 | 2.724 | 2.316 |
| | SD | 0.282 | 0.140 | 0.206 | 0.179 | 0.167 | 0.151 | 0.200 | 0.253 | 0.123 | 0.301 |
| | Min | 1.300 | 2.206 | 1.957 | 2.114 | 2.129 | 2.200 | 1.744 | 1.779 | 2.451 | 1.612 |
| | Max | 2.741 | 2.753 | 3.052 | 2.993 | 2.895 | 2.856 | 2.871 | 3.031 | 2.967 | 2.804 |
| | Ppk | 0.91 | 2.37 | 1.59 | 1.68 | 1.89 | 2.13 | 1.57 | 1.14 | 2.10 | 0.91 |
| | Visual | Accept | | Accept | | Accept | | Accept | | Accept | |
| 293-5 | Ave. | 2.331 | 2.368 | 2.433 | 2.358 | 2.469 | 2.265 | 2.239 | 2.384 | 2.406 | 2.541 |
| | SD | 0.302 | 0.191 | 0.176 | 0.200 | 0.087 | 0.250 | 0.251 | 0.158 | 0.165 | 0.237 |
| | Min | 1.354 | 1.874 | 2.017 | 1.962 | 2.283 | 1.697 | 1.694 | 2.014 | 2.015 | 1.812 |
| | Max | 2.722 | 2.670 | 2.731 | 2.702 | 2.638 | 2.765 | 2.701 | 2.752 | 2.691 | 2.888 |
| | Ppk | 0.92 | 1.51 | 1.77 | 1.43 | 3.69 | 1.02 | 0.98 | 1.87 | 1.83 | 1.35 |
| | Visual | Accept | | Reject: holes/ pleats | | Reject: holes/ pleats | | Reject: holes/ pleats | | Reject: holes/ pleats | |
| 293-6 | Ave. | 2.475 | 2.429 | 2.375 | 2.318 | 2.390 | 2.424 | 2.429 | 2.545 | 2.562 | 2.487 |
| | SD | 0.187 | 0.089 | 0.110 | 0.108 | 0.076 | 0.098 | 0.128 | 0.146 | 0.129 | 0.153 |
| | Min | 1.832 | 2.232 | 2.102 | 1.866 | 2.248 | 2.273 | 2.126 | 2.146 | 2.338 | 2.138 |
| | Max | 2.739 | 2.602 | 2.590 | 2.498 | 2.559 | 2.657 | 2.616 | 2.787 | 2.877 | 2.803 |
| | Ppk | 1.73 | 3.47 | 2.66 | 2.52 | 3.92 | 3.15 | 2.42 | 2.19 | 2.42 | 2.15 |
| | Visual | Accept | | Accept | | Accept | | Accept | | Accept | |
| 293-7 | Ave. | 1.741 | 1.964 | 1.835 | 1.992 | 1.912 | 1.997 | 2.031 | 1.936 | 1.938 | 1.773 |
| | SD | 0.134 | 0.104 | 0.162 | 0.126 | 0.086 | 0.096 | 0.087 | 0.123 | 0.117 | 0.213 |
| | Min | 1.401 | 1.761 | 1.322 | 1.487 | 1.718 | 1.693 | 1.872 | 1.632 | 1.691 | 1.276 |
| | Max | 2.016 | 2.166 | 2.155 | 2.212 | 2.115 | 2.188 | 2.258 | 2.120 | 2.150 | 2.105 |
| | Ppk | 0.60 | 1.49 | 0.69 | 1.30 | 1.60 | 1.72 | 2.03 | 1.18 | 1.25 | 0.43 |

Ave.: average;
SD: standard deviation;
Min: minimum;
Max: maximum;
Ppk: process performance index An acceptance criterion for ultrasonic seal strength for a baffle member for a urostomy pouch was set between a lower specification limit (LSL) of about 1.5 lb./in to an upper specification limit (USL) of about 3.5 lb./in. Ppk is a process performance index. Ppk=min[(USL−Ave)/(3*SD), (Ave−LSL)/(3*SD)]. One of ordinary skill in the art would understand that the greater the Ppk value, better the process control, and thus, better quality products with less defects. In the ultrasonic welding process of the baffle member, the target Ppk was set at 1.33 or higher.

As shown in the ultrasonic seal strength data in TABLE 2, the samples of Film#293-6, which included an inner layer having a thickness of about 29 μm and comprising about 90 wt. % Borealis® RD735CF (polypropylene) and about 10 wt. % Hybrar® 7125 (styrene isoprene block copolymer), and an outer layer having a thickness of about 29 μm and comprising about 99 wt. % Lotryl® 18MA02 (EMA) and about 1 wt. % Polybatch® SAB1982VA (antislip master batch), passed all acceptance criteria including visual inspections and had surprisingly high Ppk values ranging from 1.73 to 3.92, which were substantially better than the other film samples.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. In an apparatus comprising a pouch for collecting biological fluids, the pouch comprising:
   a body side wall and a distal side wall defining a collection chamber therebetween;
   an inlet opening provided in the body side wall; and
   a baffle member arranged in the collection chamber, the baffle member formed from two sheets of a multilayer film, wherein the multilayer film includes an inner layer formed from a first thermoplastic composition comprising polypropylene and an outer layer formed from a second thermoplastic composition, wherein the second thermoplastic composition has a melting temperature that is at least 5° C. lower than a melting temperature of the first thermoplastic composition, wherein the two sheets are arranged such that the inner layers face each other and the outer layers face the body side wall and the distal side wall, wherein the inner layers are attached to each other and each of the outer layers is attached to the body side wall or the distal side wall;

wherein the improvement comprises the first thermoplastic composition comprising a blend of about 70 wt. % to about 99 wt. % polypropylene and about 1 wt. % to about 30 wt. % styrenic block copolymer, and the second thermoplastic composition comprising at least about 90 wt. % of a thermoplastic polymer selected from low density polyethylene (LDPE), linear low density polyethylene (LLDPE), ethylene vinyl acetate (EVA), ethylene methyl acrylate copolymer (EMA), atactic polypropylene (PP), and polypropylene-polyethylene (PP-PE) copolymer, wherein the first thermoplastic composition is configured for sealing the inner layers together via a ultrasonic welding, and the second thermoplastic composition is configured for heat sealing the outer layers to the body side wall or the distal side wall.

2. The pouch of claim 1, wherein the multilayer film is a two layer film, the inner layer comprising about 85 wt. % to about 95 wt. % polypropylene and about 5 wt. % to about 15 wt. % styrene isoprene block copolymer, and the outer layer comprising about 95 wt. % to about 100 wt. % of a thermoplastic polymer selected from LDPE, LLDPE, EVA, EMA, atactic PP, and PP-PE copolymer.

3. The pouch of claim 1 wherein each of the two sheets of the multilayer film has a rectangular-like shape having similar size and dimensions, wherein the two sheets are arranged over each other such that the inner layers of the sheets face each other and outer layers face the body side wall or the distal side wall, wherein the two sheets are ultrasonically sealed to each other about their longitudinal edges to form a tubular-shaped baffle member.

4. The pouch of claim 3, wherein each of the ultrasonically sealed edges has a seal strength of about 1.5 lb./in to about 3.5 lb./in when tested using a tensile testing machine at a constant separation rate of about 12.0±0.5 in/min.

5. The pouch of claim 1, wherein each of the two sheets is heat sealed to the body side wall or the distal side wall via at least one attachment line.

6. The pouch of claim 5, wherein one of the two sheets is heat sealed to the body side wall via a pair of attachment lines, which are generally linear and non-parallel with a wider distance between them at lower ends than at upper ends, wherein the attachment lines are curved smoothly proximate end portions in an obtuse angle, wherein the attachment lines are symmetrical about a longitudinal center line of the pouch.

7. The pouch of claim 5, wherein one of the two sheets is heat sealed to the distal side wall via a single continuous attachment line including smooth radiused upper and lower portions.

8. The pouch of claim 1, further including an anti-reflux film provided in an upper portion of the pouch between the body side wall and the distal side wall.

9. The pouch of claim 1, further including a valve provided at an opening in a bottom end of the pouch.

10. The pouch of claim 1, wherein the pouch is a urostomy pouch configured to collect liquid body waste.

11. In a method of making a pouch for collecting biological fluids, comprising the steps of:

forming a pouch including a body side wall, a distal side wall and a collection chamber defined therebetween;
providing an inlet opening in the body side wall; and
providing a baffle member, wherein the baffle member is formed using two sheets of a multilayer film, the multilayer film including an inner layer formed from a first thermoplastic composition comprising polypropylene and an outer layer formed from a second thermoplastic composition, wherein the second thermoplastic composition has a melting temperature that is at least 5° C. lower than a melting temperature of the first thermoplastic composition, wherein the two sheets are arranged such that the inner layers face each other and the outer layers face the body side wall and the distal side wall, wherein the improvement comprises providing the baffle member including the inner layer formed from a blend comprising about 70 wt. % to about 99 wt. % polypropylene and about 1 wt. % to about 30 wt. % styrenic block copolymer, and the outer layer comprising at least about 90 wt. % of a thermoplastic polymer selected from low density polyethylene (LDPE), linear low density polyethylene (LLDPE), ethylene vinyl acetate (EVA), ethylene methyl acrylate copolymer (EMA), atactic polypropylene (PP), and polypropylene-polyethylene (PP-PE) copolymer, wherein the first thermoplastic composition is configured for sealing the inner layers together via a ultrasonic welding, and the second thermoplastic composition is configured for heat sealing the outer layers to the body side wall or the distal side wall, wherein the step of forming the baffle member includes sealing the sheets along their longitudinal peripheral edges via ultrasonic welding to form a tubular baffle member.

12. The method of claim 11, wherein the sheets are ultrasonically sealed together such that each of the sealed peripheral edge has a seal strength of about 1.5 lb./in to about 3.5 lb./in when tested using a tensile machine at a constant separation rate of about 12.0±0.5 in/min.

13. The method of claim 11, further including arranging the baffle member in the collection chamber such that the outer layer of one of the sheets is adjacent the body side wall and the outer layer of the other sheet is adjacent the distal side wall, and heat sealing one of the sheets to the body side wall, and heat sealing the other sheet to the distal side wall via at least one attachment line.

14. The method of claim 13, wherein one of the sheets is heat sealed to the body side wall via a pair of attachment lines, which are generally linear and non-parallel with a wider distance between them at lower ends than at upper ends, wherein the attachment lines are curved smoothly at respective ends at an obtuse angle, wherein the attachment lines are symmetrical about a longitudinal center line of the pouch.

15. The method of claim 13, wherein one of the sheets is heat sealed to the distal side wall via a single continuous attachment line including smooth radiused upper and lower portions.

16. The method of claim 11, wherein the baffle member is formed using a two layer film, the inner layer comprising about 85 wt. % to about 95 wt. % polypropylene and about 5 wt. % to about 15 wt. % styrene isoprene block copolymer, and the outer layer comprising about 95 wt. % to about 100 wt. % of a thermoplastic polymer selected from LDPE, LLDPE, EVA, EMA, atactic PP, and PP-PE copolymer.

* * * * *